United States Patent [19]

McConnell et al.

[11] Patent Number: 4,786,472
[45] Date of Patent: Nov. 22, 1988

[54] AIR SAMPLING DEVICE

[75] Inventors: Bain C. McConnell; Guy B. Oldaker, III; Richard F. Walsh, all of Winston-Salem, N.C.

[73] Assignee: R. J. Reynolds Tobacco Company, Winston-Salem, N.C.

[21] Appl. No.: 899,186

[22] Filed: Aug. 21, 1986

[51] Int. Cl.[4] .................. G01N 7/02; G01N 31/00
[52] U.S. Cl. .................................. 422/61; 422/88; 422/119; 436/106; 436/134; 73/863.21; 73/863.23; 73/23
[58] Field of Search .............. 422/61, 83, 88, 119; 436/106, 134, 175, 177, 178, 181; 73/23, 863.21, 863.23, 863.31, 29

[56] References Cited

U.S. PATENT DOCUMENTS

| | | | |
|---|---|---|---|
| 3,507,147 | 4/1970 | Llewellyn | 73/863.21 |
| 3,871,827 | 3/1975 | Seiler et al. | 422/83 |
| 3,903,745 | 9/1975 | Bolser | 73/863.21 |
| 4,324,146 | 4/1982 | Born | 73/863.21 |
| 4,569,235 | 2/1986 | Conkle et al. | 73/863.23 |

*Primary Examiner*—Benoît Castel

[57] ABSTRACT

A briefcase contains components capable of sampling air for analysis. For example, air can be introduced into the briefcase through inlet ports and that air can be monitored for components of environmental tobacco smoke. A chemical collection device such as a sorbent tube can collect nicotine, a filter can collect respirable suspended particulate matter, and a chemical detector can monitor carbon monoxide levels. The environmental temperature and barometric pressure of the environment can be monitored also. Data is stored on a microcomputer within the briefcase, and can be transferred to a computer at a later time for data analysis.

18 Claims, 3 Drawing Sheets

AIR SAMPLING DEVICE

BACKGROUND OF THE INVENTION

This invention relates to atmospheric or air sampling devices, and in particular to air sampling devices having a portable size.

Atmospheric air, either indoors or outdoors, contains gaseous material and particulate matter. For example, air which is inhaled by human beings typically includes gases such as nitrogen, oxygen and carbon dioxide; water vapor; and particulate material such as dust, spores, and the like.

Recent interest towards studying the nature, characteristics and quality of environmental air has developed. Of particular interest is the study of indoor settings in order that steps toward providing effective ventilation, and/or air circulation or recirculation can be taken. For example, it is desirable to study environmental air in industrial areas such as factories, chemical plants and warehouses; in agricultural areas such as barns and silos; in social areas such as hotels, auditoriums and stores; and in personal areas such as homes and apartments. In particular, it is desirable to sample and analyze environmental air for asbestos fibers, dust, volatile organic compounds, pollen, coal dust, gasoline or diesel engine exhaust, smoke, wood stove or furnace exhaust, or metal ions or materials such as lead, beryllium, cadmium, uranium, zinc or selenium.

It is desirable to collect and analyze environmental air samples in a particular setting over a fairly long period of time. However, for a realistic and representative assessment of the environmental air, it is often necessary to measure several substances over a range of known conditions. Unfortunately, the sampling and collection of environmental air samples often involve the use of noisy, large, obtrusive equipment. Such types of equipment often do not provide realistic or representative assessments of a particular setting due to the fact that the obtrusive nature of the equipment can tend to affect human behavior during data collection periods.

It would be highly desirable to provide a portable, self-contained air sampling device which is capable of monitoring a number of substances under dynamic conditions over a continuous period of time.

SUMMARY OF THE INVENTION

This invention relates to an environmental air sampling device which includes (a) a portable outer container having at least one air inlet means;

(b) calibrated air flow pumping means connected to the air inlet means;

(c) at least one chemical collection means and/or detection means for quantitative determination of predetermined chemicals;

(d) means for sampling predetermined particulate matter;

(e) means for determining relative conditions of environment;

(f) data storage means including means for recording time periods over which air is sampled, means for recording relative conditions of environment, and means for recording data provided from the chemical detection means; and (g) power source for operation of components including the pumping means and data collection means.

This invention provides an efficient and effective means for sampling atmospheric air for analysis. Of particular interest is environmental air which is present at a particular location and to which a human may be exposed. Of special interest is air which is located in public and private indoor environments. Such environments include homes, apartments, motel rooms, offices, stores, lobbies, restaurants, auditoriums, factories, laboratories, warehouses, barns, aircraft cabins, automobiles, and the like.

The device of this invention provides a flexible system for sampling air in a wide variety of indoor environments. The portable device is self contained, is easily operated, and is unobtrusive. The device can measure more than one substance as well as relative conditions of the environment such as temperature, relative humidity and atmospheric pressure. The device can be operated over relatively long periods of time. Thus, it is possible to monitor environmental air for predetermined substances on a continuous basis while having the ability to identify short term changes in concentration of particular substances.

The device of this invention is useful for assessing the quality of environmental air for industrial hygiene studies, in assessing the efficiency of exhaust and/or air filtration systems, for identifying and quantifying components of environmental air, in assessing the performance of heaters, stoves or air conditioners, or other such purposes. In addition, the portable nature of the device allows a person to carry the device thereby providing for the ability to assess or estimate that person's exposure to predetermined substances.

The device of this invention is particularly useful for sampling atmospheric air which contains environmental tobacco smoke which is provided from lighted cigarettes, cigars and pipes. Of special interest is a device capable of reliably sampling environmental air for nicotine, carbon monoxide and respirable suspended particulate matter. The reliable sampling of environmental air provides data for analysis.

DETAILED DESCRIPTION OF THE EMBODIMENTS

Figure 1:
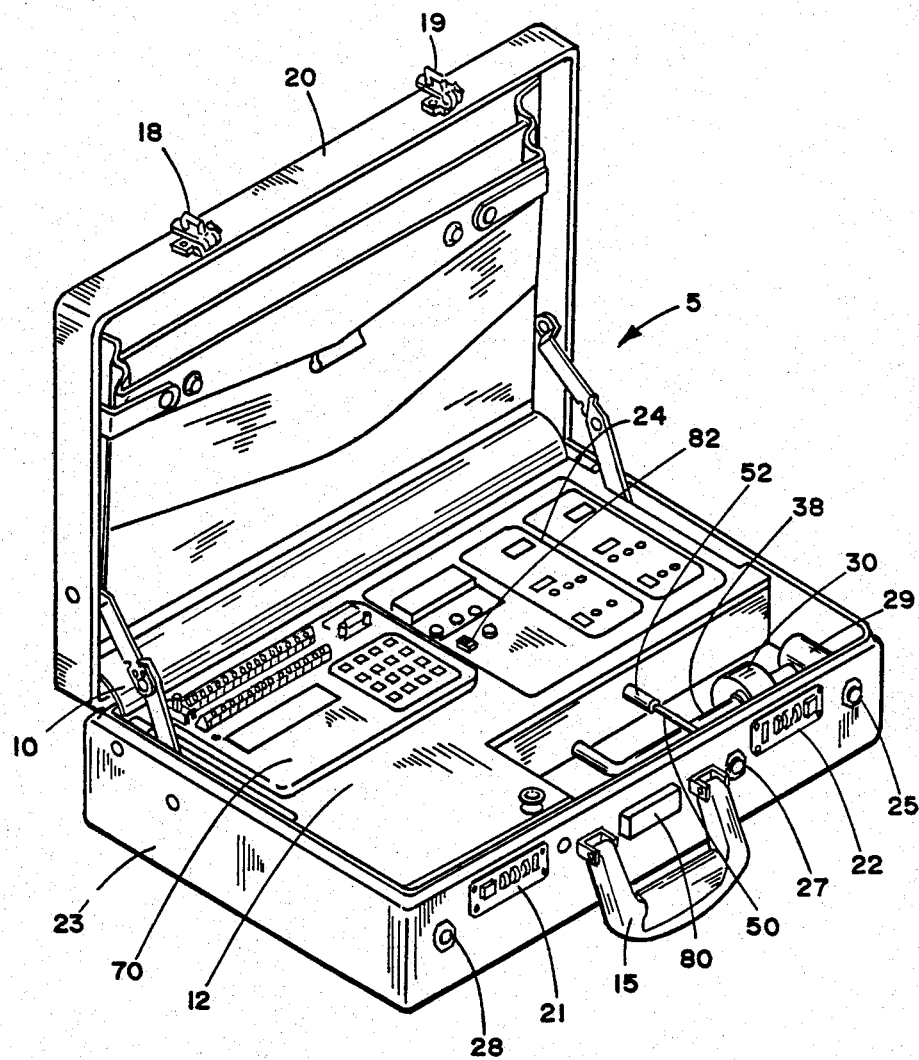
FIG. 1 is a perspective of a configuration of the air sampling device showing an open briefcase and the various components contained therein.
Figure 2:
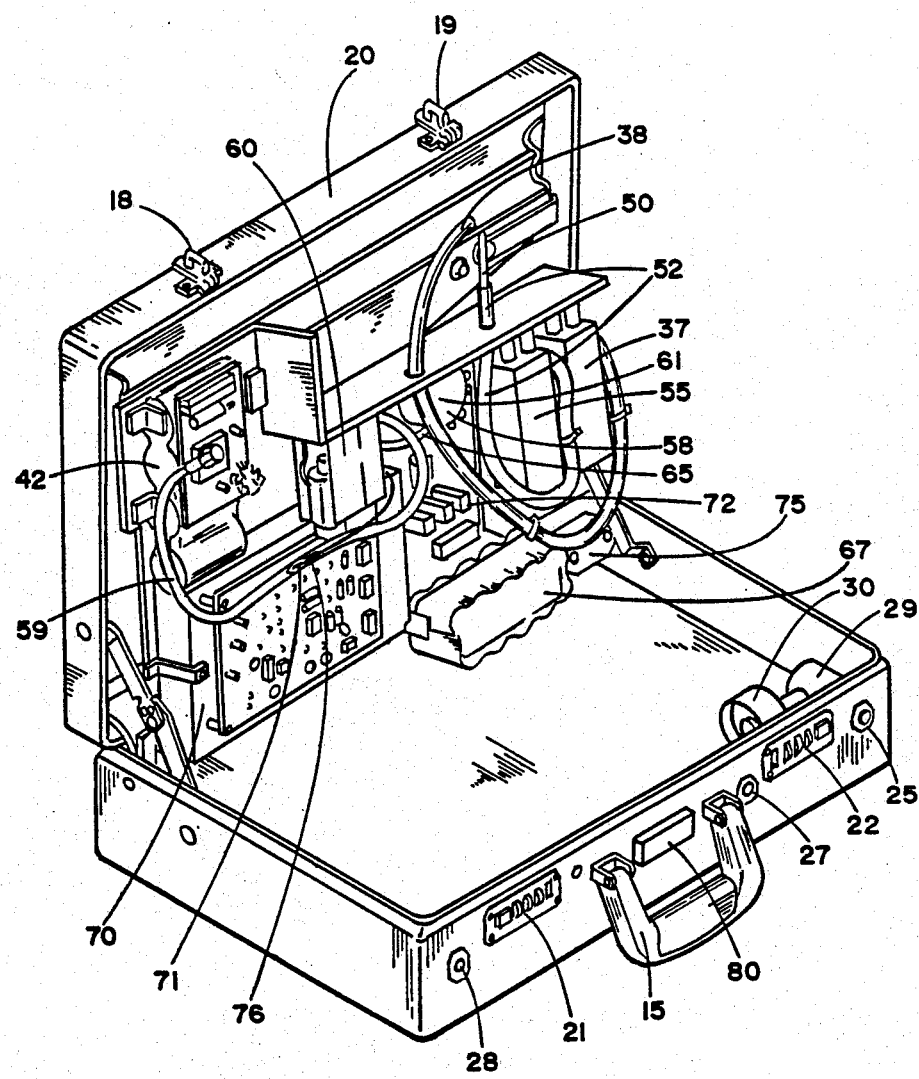
FIG. 2 is a perspective of the configuration shown in FIG. 1 showing the inner frame rotated upwards in order to expose the various components which are contained within the briefcase.

Referring to FIGS. 1 and 2 air sampling device 5 includes container 10 such as a briefcase or other portable container which allows for easy movement of the components of the device as well as providing a carrying means for the various components. An example of a suitable container is a hard sided leather briefcase available from National Luggage of Montreal, Canada; and having outer dimensions of 12.75 inch width, 17.75 inch length and 4.75 inch thickness. Preferably, an inner frame 12 such as a machined polymethylmethacrylate sheet keeps the various components in place. Alternatively, molded polyurethane foam, or other such means can hold the various components in place. The briefcase includes a carrying means 15 such as handle or the like.

The briefcase can be opened with hinges (not shown), and is maintained closed using locking means such as a pair of latches 18 and 19 attached to the movable top portion 20 which lock with locking means 21 and 22 at the bottom portion 23. Preferably, the briefcase opens to leave a bottom portion which contains the various components. When open, a sampling system control panel 24 is exposed. The control panel allows the user to operate various components and view evidence of the operation of the underlying components.

The container 10 is portable. By the term "portable" is meant that the container is of a relatively small size, preferably of a size and weight which can be lifted and carried by an adult human being. Generally, a portable air sampling device 5 weighs less than about 50 pounds, preferably less than about 30 pounds, more preferably less than about 20 pounds, and has the size (i.e., volume) which approximates that of a briefcase. A preferred air sampling device weighs about 16 pounds.

In operation, the air sampling device preferably is employed with the container in closed or shut form. Air is introduced to the air sampling components by air inlet means such as inlet ports 25, 27 and 28. The air inlet ports are positioned near the handle and locking means of the briefcase in a suitable position for air intake. Suitable air inlet ports 27 and 28 are Swagelok brass bulk head reducer tube fittings (Catalogue No. B-400-R1-4) which are manufactured by Crawford Fitting Co. of Solan, Ohio, U.S.A. Typically, the outer portions of the ports are machined and polished to a square or circular shape for aesthetic purposes. In addition, it is desirable to conceal the inlet means essentially flat against the outer surface of the briefcase. Typically, the air inlet ports 27 and 28 are provided by tubing having an inner diameter of about ¼ inch. The air inlet port 25 which provides for the sampling of particulate matter preferably extends about ⅛ inch from the outer surface of the briefcase. The inlet port 25 is preferably a ¼ inch inner diameter tube which is the inlet portion of a commercially available Five Micrometer Impactor 29 which is sold by T.S.I. Inc. of St. Paul, Minn., U.S.A.

The impactor 29 serves to separate large size particles while allowing particulate matter of the desired size range (i.e., predetermined particulate matter) to be collected. For example, the aforementioned impactor is advantageously used in order to provide for the sampling (e.g., collection) of particulate matter which is provided from environmental tobacco smoke. In such a situation, undesirable large size particulate matter is separated from the smaller size particulate matter which is desired to be collected. For example, for the sampling of environmental tobacco smoke, an impactor can be selected to remove particles having aerodynamic mean diameters greater than 3.5 micrometers.

The particulate matter passing through the impactor 29 is collected in a filter means 30 which is connected to the impactor. Typically, respirable suspended particulate matter provided from environmental tobacco smoke can be collected on a circular, 37 mm diameter Fluoropore membrane filter which is a polytetrafluoroethylene film having a pore size of 1 micrometer which is available under Catalogue No. FALP 03700 from Millipore Corp., Bedford, Mass., U.S.A. The filter is provided in a plastic filter cassette. Such a filter cassette is commercially available as Catalogue No. M00037PO from Millipore Corp. After the sampling of particulate matter is complete, the membrane filter can be removed from the filter cassette, and analysis (e.g., chemical analysis) of the collected material can be performed using any suitable technique.

The filter means is connected to pumping means 37 by tube 38. A suitable pumping means is a quietly running constant flow pump commercially available as Universal Flow sample Pump Series 224 by SKC Inc., Eighty Four, Pa., U.S.A. The constant flow pumps provide a calibrated air flow pumping means. A suitable tube 38 has an inner diameter of ¼ inch and is commercially available as Tygon by Norton Co., Akron, Ohio, U.S.A.

The constant flow pump is powered by power source 42. A suitable power source is a 4.8 volt source provided by Four Panasonic "F" type composite nickel cadmium Model P-440DE batteries. The power source 42 can be equipped with any conventional recharging unit. The recharging unit includes a recharging circuit 44 and a power source (not shown). A suitable power source is a Model 820A4465 Wall Plug-In Power Source which is commercially available from Pan-Magnetics International, Inc., Carson, Calif.

An inlet port 27 is connected to a chemical collection means 50 such as a glass sorbent tube having a suitable absorbent composition. A preferred sorbent tube 50 has a diameter of 6 mm and a length of 70 mm. Preferably, the glass sorbent tube is protected within the inlet port 27 by a protective collar or casing, or the like. A preferred tube for collection of nicotine is commercially available as Sorbent Tube, Catalogue No. 226-30-11-04, Model XAD-4 by SKC, Inc., Eighty Four, Pa., U.S.A. Similar sorbent tubes are available for collecting halogen containing chemicals such as chlorobenzene, carbon tetrachloride, bromoform, ethyl bromide, chloroprene and epichlorohydrin; and other organic chemicals such as benzene, acrylonitrite, various alkanes, ethers and alcohols, aniline, napthalene, xylenes, carbon disulfide, kerosene, and the like. The sorbent tube is positioned in inlet port 27 such that air passes through the sorbent tube and out of the sorbent tube through 3/16 inch inner diameter connection Tygon tube 52 through a second pump 55. A suitable pump is described hereinbefore. The second pump 55 is powered by power source 42 in a manner described hereinbefore. After he sorbent tube has been subjected to use, the open ends of the sorbent tube can be covered with a sealing means such as a cap. Analysis for the collected chemical (e.g., nicotine) can be performed using known chemical analysis techniques.

Air from inlet port 28 is passed through a Tygon tube 59 to a third pump 60 which is available as Model No. 10037 from Gillian Instrument Co., Wayne, N.J. The third pump passes air from the inlet port to a chemical detection means such as a carbon monoxide detector. A suitable detection means is a sensor such as an electrochemical cell 61 whereby the oxidation of carbon monoxide is accompanied by a voltage signal. A suitable carbon monoxide detector is a Model Otox 2001 available from Neotronics Ltd., Gainesville, Ga., U.S.A. In particular, the commercially available chemical detection sensor is removed from the circuit board 63 and a cover 61 supplied by the manufacturer is mounted over the sensor (as shown in FIG. 2). The covered sensor 61 is then connected to the aforementioned pump using Tygon tubing 65. The detection means is powered by a second power source 67 which is advantageously a 12 volt source provided by ten Panasonic "F" Type composite nickel cadmium Model P-60AAE batteries. The circuit board 63 is mounted under the data storage means 70. Another example of a carbon monoxide detection means is a Carbon Monoxide Detector Model 15ECS3C03 available from General Electric, Wilmington, Mass., U.S.A.

The carbon monoxide detection means can be operated at a flow rate which can be set by manual adjustment of a potentiometer 72. A suitable potentiometer is a 500 ohm potentiometer which positioned between the third pump 60 and the second power source 67 thereby controlling the flow rate at which air passes through the detection means. In this manner, the lifetime of the power source 67 can be extended.

Data concerning the instantaneous concentration of a chemical such as carbon monoxide are stored in the data storage or collection means 70 which will be described in greater detail hereinafter. For example, a voltage signal which is produced by the oxidation of carbon monoxide by the chemical detection means 61 is stored in the data storage means 70. Preferably, data from the chemical detection means are obtained and stored over discrete periods of time (e.g., at about 1 minute intervals).

Relative conditions of the environment during air sampling are recorded. For example, instantaneous environmental temperature values are determined using temperature sensing means 71 such as a thermistor which is commercially available as Model No. 107 Temperature Probe by Campbell Scientific, Inc., Logan, Ut., U.S.A. Such a thermistor can be conveniently positioned inside the Tygon tube 59 (which is shown as partially cut away in FIG. 2) which leads to the chemical detection means. Additionally, instantaneous barometric pressure values are determined using barometric pressure sensing means 75 such as a commercially available Barometric Pressure Transducer Series PX140 by Omega Engineering, Inc., Stamford, Conn., U.S.A. If desired (i.e., optionally), relative humidity can be monitored using a MP-100F Relative Humidity Probe available from Rotronic Instrument Corp., Huntington, N.Y., U.S.A. (not shown). Atmospheric pressure and temperature data collection is desirable due to the fact that the collected data concerning various chemicals and particulate matter are usually temperature and pressure dependent. Preferably, data from the aforementioned components are obtained and stored over discrete periods of time (e.g., at about 1 minute intervals).

Data storage means 70 provides for the collection and storage of data relating to the time that the air sampling device is in operation, instantaneous barometric pressure (as provided by the transducer 75), instantaneous temperature values (as provided by the thermistor), the values received from the carbon monoxide detection means 61 (for determining the concentration of carbon monoxide), time periods over which known quantities of air pass through the respective pumps, (for determining the volume of air sampled), the amount of voltage employed in operating the pumps, and the like. An example of a suitable data storage means is a commercially available 21X Micrologger supplied by Campbell Scientific, Inc., Logan, Ut., U.S.A. The data collection means is powered by previously described, second power source 67. The separate power sources for the data storage means and pumps are employed in order to assure that the data storage means continuously has a source of power. In the preferred embodiment, the previously described temperature sensing means is connected to the data storage means by connecting means 76 and barometric pressure sensing means is connected to the data storage means thereby receiving power from the second power source 67.

The container preferably is closed during operation and the pumps and chemical detection means are activated using an on/off switch 80 located on the outer region of the container.

A calibration switch 82 is employed in order to provide for calibration of pumps 37, 55 and 60, and the chemical detection means 58. The calibration switch is connected to all electrically operated components, and provides normal system operation except that data storage in the data storage means 70 is inhibited.

In operation, the air sampling device is employed in the desired environment for the desired period of time.

Data are recorded using the data storage means. For example, the time period over which the device is operated (i.e., over which the air is sampled) is recorded. In particular, the timing means can record the time at which the device is turned on as well as the time at which the device is turned off. The method for providing and calibrating the timing means can vary and is within skill of the ordinary artisan. The data storage means can record the voltage of the power source of the constant flow pumps in order to ensure that pumps can operate for a predetermined sampling period and consequently that an accurate determination of the volume of air tested can be made. Information provided from the chemical detection means (e.g., concerning the concentration of carbon monoxide in the sampled air) can be recorded on the data storage means. In addition, instantaneous data concerning the temperature and pressure of the environment can be recorded on the data storage means. The method for providing for the storage of the various data can vary and is within the skill of the ordinary artisan.

Figure 3:
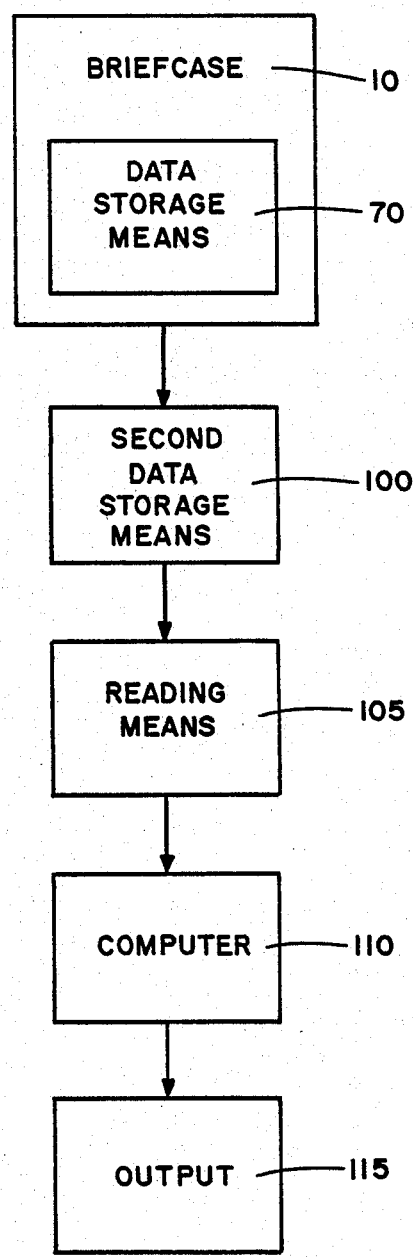
FIG. 3 shows a flowchart of the method for treating data which is entered into the data storage means.

FIG. 3 sets forth a flow diagram for obtaining data from the data storage means 70 for analysis. In particular, data recorded by the internal memory of the previously described commercially available 21X Micrologger contained in briefcase 10 is transferred to a separate, second data storage means 100 such as a standard audio cassette tape using a commercially available SC-93 Cassette Interface from Campbell Scientific, Inc. The cassette containing the data transferred from the data collection or storage means 70 can be stored for data analysis. For example, the cassette 100 can be operated in a cassette reading means 105 such as a commercially available C-20 cassette interface from Campbell Scientific, Inc. The cassette reading means 105 provides for data input into a computer 110 for analysis. A suitable computer is a Hewlett-Packard Model 150. The data can be analyzed as desired, and printout of the data and/or analyzed data can be obtained using output means 115 such as a conventional printer, plotting means, or the like. Of particular interest is the fact that information regarding the components of the air can be analyzed with reference to the actual instantaneous environmental conditions such as temperature and barometric pressure.

What is claimed is:

1. An environmental air sampling device which includes (a) a portable outer container having air inlet means; (b) calibrated air flow pumping means connected to the air inlet means; (c) at least one chemical collection means for quantitative determination of predetermined chemicals; (d) means for sampling predetermined particulate matter; (e) means for determining relative conditions of environment including a temperature sensing means for determining environmental temperature and a means for sensing barometric pressure; (f) data storage means including means for recording time periods over which air is sampled and means for recording relative conditions of environment; and (g) power source for operation of components including the pumping means and data storage means;

wherein components (b) through (g) are contained within the outer container and the air sampling device is adapted to be employed with the outer container in closed form.

2. The device of claim 1 wherein the outer container is a briefcase.

3. The device of claim 2 which weighs less than about 30 pounds.

4. The device of claim 1 wherein said means for sampling predetermined particulate matter is a means for collecting respirable suspended particulate matter form environmental tobacco smoke.

5. The device of claim 1 wherein said chemical collection means is a means for collecting nicotine.

6. The device of claim 1 wherein the power source includes at least one battery and a recharging unit.

7. An environmental air sampling device which includes (a) a portable outer container having air inlet means; (b) calibrated air flow pumping means connected to the air inlet means; (c) at least one chemical detection means for quantitative deterination of predetermined chemicals; (d) means for sampling predetermined particulate matter; (e) means for determining relative conditions of environment including a temperature sensing means for determining environmental temperature and a means for sensing barometric pressure; (f) data storage means including means for recording time periods over which air is sampled, means for recording relative conditions of environment, and means for recording data provided from the chemical detection means; and (g) power source for operation of components including the pumping means and data storage means;

wherein components (b) through (g) are contained within the outer container; and the air sampling device is adapted to be employed with the outer container in closed form.

8. The device of claim 7 wherein the outer container is a briefcase.

9. The device of claim 8 which weighs less than about 30 pounds.

10. The device of claim 7 wherein said means for sampling predetermined particulate matter is a means for collecting respirable suspended particulate matter form environmental tobacco smoke.

11. The device of claim 7 wherein said chemical detection means is a means for collecting carbon monoxide.

12. The device of claim 7 wherein the power source includes at least one battery and a recharging unit.

13. An environmental air sampling device which includes (a) a portable outer container having air inlet means; (b) calibrated air flow pumping means connected to the air inlet means; (c) at least one chemical detection means for quantitative determination of predetermined chemicals; (d) at least one chemical collection means for quantitative determination of predetermined chemicals; (e) means for sampling predetermined particulate matter; (f) means for determining relative conditions of environment including a temperature sensing means for determining environmental temperature and a means for sensing barometeric pressure; (g) data storage means including means for recording time periods over which air is sampled, means for recording relative conditions of environment, and means for recording data provided from the chemical detection means; and (h) power source for operation of storage including the pumping means and data collection means;

wherein components (b) through (h) are contained within the outer container, and the air sampling device is adapted to be employed with the outer container in closed form.

14. The device of claim 13 wherein said means for sampling predetermined particulate matter is a means for collecting respirable suspended particulate matter for environmental tobacco smoke.

15. The device of claim 13 wherein the outer container is a briefcase.

16. The device of claim 15 which weighs less than about 30 pounds.

17. The device of claim 13 wherein said chemical detection means is a means for detecting carbon monoxie and said chemical collection means is a means for collecting nicotine.

18. The device of claim 13 wherein the power source includes at least one battery and a recharging unit.

* * * * *